United States Patent

Tosima et al.

[11] 4,409,333
[45] Oct. 11, 1983

[54] METHOD FOR THE EVALUATION OF SOLDERABILITY

[75] Inventors: Soitiro Tosima, Machida; Shigeo Harada, Isehara, both of Japan

[73] Assignee: RCA Corporation, New York, N.Y.

[21] Appl. No.: 327,595

[22] Filed: Dec. 4, 1981

[51] Int. Cl.³ ............................................... B23K 1/00
[52] U.S. Cl. ..................................... 436/2; 436/164; 228/104
[58] Field of Search .................... 228/103, 104; 436/2, 436/164

[56] References Cited

U.S. PATENT DOCUMENTS 3,753,652  8/1973  Gassmann et al. ..................... 436/2

FOREIGN PATENT DOCUMENTS 52-29691  8/1977  Japan ................................... 228/103
55-18197  5/1980  Japan ................................... 228/103

OTHER PUBLICATIONS

Herdzik et al., IBM Technical Disclosure Bulletin, vol. 18, No. 10, 3/76, p. 3231.

*Primary Examiner*—Hiram H. Bernstein
*Attorney, Agent, or Firm*—Birgit E. Morris; Edward J. Sites

[57] ABSTRACT

A test procedure is disclosed for evaluating the solderability properties of molten solder. In the method of this invention, a testpiece is provided which has a transparent support with a film of metal such as copper deposited on one surface of the transparent support. The surface having the metal film is immersed in the molten solder and the time required for alloying to occur and be observed through the transparent support is measured to determine rate of alloying and, thereby, the solderability properties of the molten solder under evaluation.

15 Claims, 17 Drawing Figures

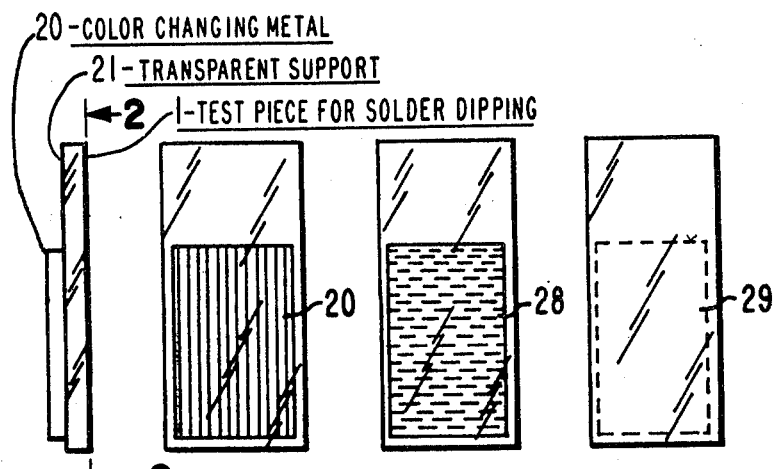
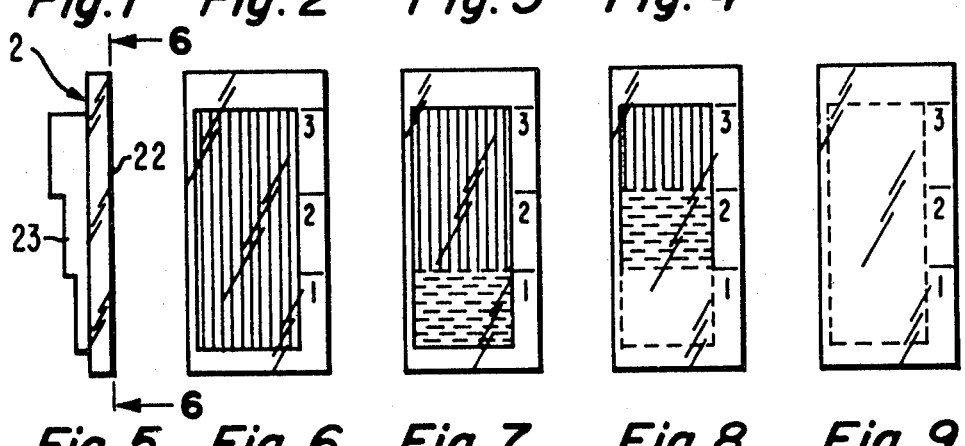
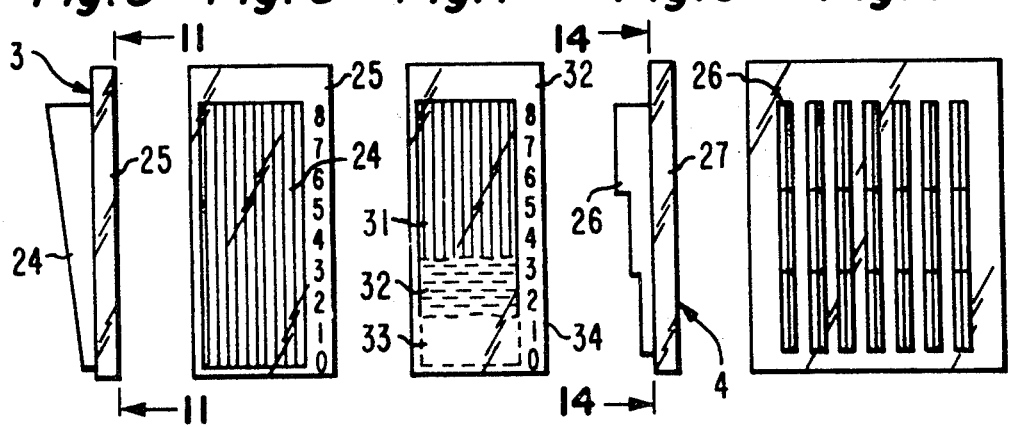

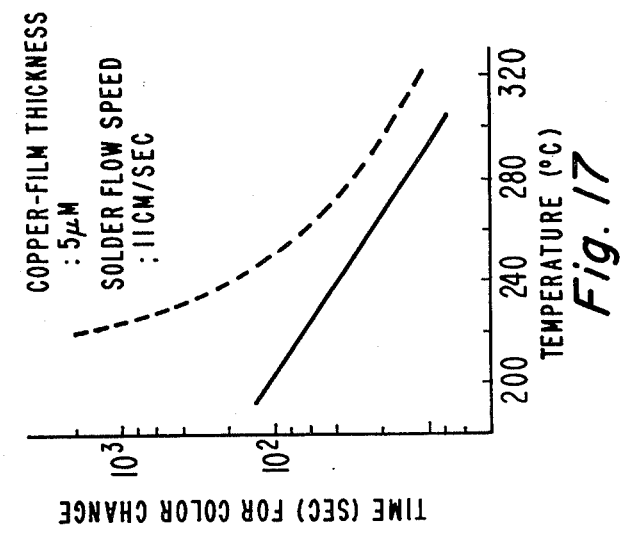
Fig. 17
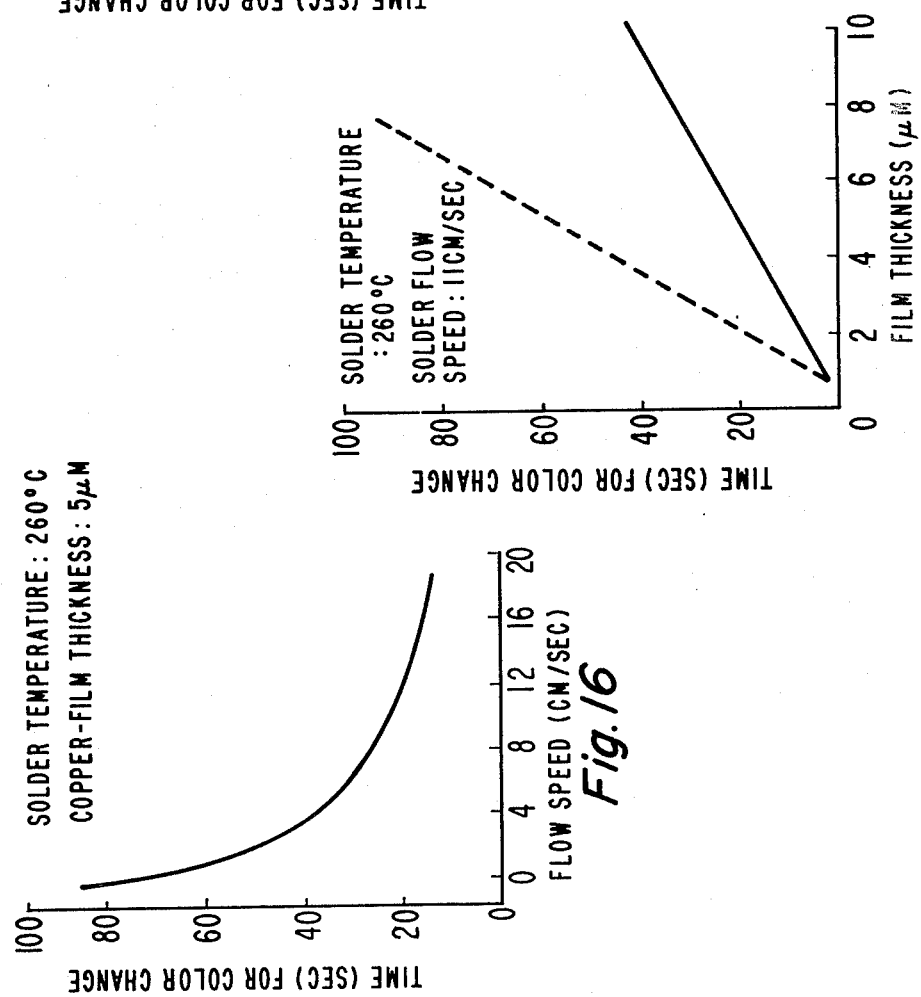
Fig. 15
Fig. 16

METHOD FOR THE EVALUATION OF SOLDERABILITY

This invention relates to a method for determining the effect of changes on solderability properties and, more particularly, with a method to determine the effect of contaminants on solder compositions.

BACKGROUND OF THE INVENTION

Soldering is a widely used assembly procedure employed in the manufacture of a variety of products. Soldering, for example, is used in the manufacture of common "tin" cans to seal the side joints, in the assembly of fine jewelry, in the manufacture of automobile bodies and the like. One of the most important uses of soldering and also one of the most critical uses with regard to the quality of the soldering required is in the assembly of electronic apparatus. Soldering is used in the assembly of the electronic apparatus to both physically hold the individual components in place as, for example, on a printed circuit board, and to provide electrical continuity in the circuitry of the apparatus. The solder connections in an electrical assembly must be properly made in order for the resulting electronic apparatus to operate as designed. The problems encountered in soldering electronic apparatus are especially difficult because even relatively simple circuits can literally have hundreds of connections, each of which must be properly soldered. It is furthermore common practice to conduct the soldering of most large circuits in a mass soldering operation wherein all the connections are soldered at the same time by dipping circuitry to be soldered in a molten pool of solder or by passing the circuitry through a wave of molten solder. Mass soldering techniques have proven to be highly successful in increasing the production rate and even in improving the quality of the soldered joints. However, the operating parameters and, particularly, the quality of the solder employed must be closely controlled in order to obtain a satisfactory soldering result on a consistent basis. The single most difficult parameter to maintain in mass soldering processes is the contamination level of the solder.

Solders are made from mixtures of different metals. The particular metal and the relative amounts of each metal in a solder composition are generally selected so as to form a eutectic mixture; that is a mixture having a melting point substantially lower than the melting point of the individual metals used to form the solder. Mixtures of selected metal, for example, lead, tin, bismuth, indium, zinc, silver and/or gold are widely used in solder compositions. The most used solder compositions are mixtures of tin and lead with solders containing about 60% tin and about 40% lead being the principal type of solders used in the soldering of electronic assemblies.

Each solder composition has a certain specific metal composition at which optimum soldering properties are obtained. The presence of even minor amounts of certain metals as impurities can, and often does, have a substantial adverse effect on the solderability properties of the composition. It has been found, however, that it is very difficult to prevent the contamination of the solders, especially in mass soldering processes, such as dip-soldering or wave-soldering, in that the pool of solder is gradually contaminated as a result of material introduced with the circuitry to be soldered, atmospheric impurities and the like. One of the principal sources of metal impurities in solder compositions has been found to be copper, which is inherently removed from circuit boards during the soldering process.

It is recognized that it is important to monitor the solder quality and to maintain solder above certain minimum contamination levels in order to maintain consistent good soldering quality. However, the test methods heretofore proposed for monitoring solder quality were generally unsatisfactory, especially under production conditions. It was suggested, for example, among other things, that the solder be spectrographically analyzed for metal contamination and, particularly, for the presence of certain metallic impurities such as copper. This, however, required relatively expensive test apparatus and required a skilled technician to conduct the evaluation. Furthermore, the test was relatively time-consuming so that often the soldering process was out of control before the test results were obtained. Other suggestions were to measure certain physical properties such as surface tension and the like. The physical measurements, at best, have proven to be highly unreliable. The inability to make a fast, simple and accurate evaluation of the solderability properties has resulted in substantial production losses due to poor soldering.

Solderability problems are also encountered when virgin soldering compositions are used, if changes are made in the process parameters employed in the soldering apparatus, such as changing the temperature of the solder, the soldering rates, fluxes and the like. These changes have a substantial effect on the quality of the resulting soldered connections.

What would be highly desirable would be a relatively simple, fast and accurate process for evaluating solder compositions as to their soldering properties and the effect of process changes on soldering properties.

BRIEF DESCRIPTION OF THE INVENTION

A test procedure is provided in accordance with this invention for evaluating the solderability of solder compositions. The evaluation utilizes a transparent support, such as a clear glass plate, on which there is deposited on one surface thereof a thin film of a metal such as copper. The surface of the support, having the metal film deposited on it, is immersed in a pool of the molten solder to be evaluated for a measured length of time. The metal film in contact with the solder will form an alloy with the solder which preferably results in a color change of the metal film on the support and, eventually, in the dissolution of the metal film from the support into the solder. The time required for the color change due to alloying of the solder with the metal film on the support, and/or the time required for complete dissolution of the metal film from the support are measured. The solderability quality of the solder is then directly determined by the rate of alloying and/or the rate of dissolution of the metal film from the transparent support with a known standard.

BRIEF DESCRIPTION OF THE DRAWINGS

FIG. 1 is a side view of a first embodiment of a metal-coated test piece suitable for use in the method of this invention.

FIG. 2 is an illustration of the test piece of FIG. 1, taken as indicated by the arrows 2 on FIG. 1.

FIG. 3 is an illustration of the test piece of FIG. 2 after being subjected to contact with a molten solder bath and undergoing alloying.

FIG. 4 is an illustration of the test piece of FIG. 2 after having the metal coating completely removed.

FIG. 5 is a side view of an alternate type of test piece for use in the method of this invention which has a stepped film of metal deposited on the surface thereof.

FIG. 6 is an illustration of the test piece of FIG. 5, taken as illustrated by the arrows 6 on FIG. 5.

FIG. 7 is an illustration of the test piece of FIG. 6 which has been subjected to contact with a solder bath and has the metal film thereon partially alloyed.

FIG. 8 is an illustration of the test piece of FIG. 6 which has been contacted with a molten solder bath and which has the film thereof partially alloyed and partially dissolved.

FIG. 9 is an illustration of the test piece of FIG. 6 in which the metal film has been completely removed.

FIG. 10 is a side view of a further alternate embodiment of a test piece for use in the method of this invention having a wedge-shaped metal film on the surface thereof.

FIG. 11 is an illustration of test piece of FIG. 10 taken as indicated by the arrows 11 on FIG. 10.

FIG. 12 is an illustration of the test piece of FIG. 11 having the metal film on the surface thereof partially alloyed and partially dissolved.

FIG. 13 is a side view of yet a further embodiment of a test piece suitable for use in the method of this invention which is especially adapted for use in evaluating icicling and bridging properties of solders.

FIG. 14 is an illustration of the test piece of FIG. 13 taken as indicated by the arrows 14 on FIG. 13.

FIG. 15 is a graph comparing the thickness of the metal film and the time required for the color changes indicating alloying.

FIG. 16 is a graph comparing flow speed of the solder and time required for color change due to alloying.

FIG. 17 is a chart comparing the temperature of the molten solder bath with the time required for a color change indicating alloying.

DETAILED DESCRIPTION OF THE INVENTION

In describing the present invention, specific attention will be directed to the soldering of copper with a tin-lead alloy solder such as is commonly used in the manufacture of electronic apparatus as this is an extremely important area of use for the present invention. It should be appreciated, however, that the method of the present invention is also applicable to other products and other metal and solder combinations and that these, likewise, are included within the scope of the present invention.

The initial step in the method of this invention is to provide the test pieces for use in the evaluation. The test pieces are comprised of a transparent support which has a thin film of metal deposited on one surface thereof. The support should preferably be made of a water-white transparent material. The support must also be capable of withstanding the temperature of the molten solder pool which is typically between 190° and 320° C. Various materials can be used as the support providing they meet the above noted requirements. It has been found that borosilicate glass is especially useful as the support for test pieces used in the present invention.

The thickness of the transparent support has to be selected with a certain degree of care. The support must be sufficiently thick that it can withstand the physical handling involved in the test procedure. The support, however, must not be excessively thick in that it may have a heat capacity which will locally cool the solder under test and cause a distortion of the test results. Ideally, the substrate should have a thickness such that it will reach thermal equilibrium within a few seconds with the solder pool under evaluation. For most glass supports, such as borosilicate glass supports, a thickness between 0.20 and 0.30 mm is satisfactory with about 0.26 mm appearing to be an optimum thickness.

As noted above, a thin layer of metal is deposited on one side of the transparent support so that the film of metal can be observed through the support. The metal layer, which is formed on the support, is preferably a metal which has a color in the state in which it is applied to the transparent support which is optically distinguishable from the alloy composition formed with the metal of the solder during the test. Several metals which have been found to be especially useful in forming alloys of a different color with the solder commonly employed are copper and gold. Copper is especially useful as the metal to be deposited on the transparent support as, when it is applied, it has a distinctive reddish color (represented on the figures by color hatching) and when it is alloyed with, for example, the tin of a lead-tin solder, forms a brilliant silver-white alloy (represented on the figures by color hatching).

The film of metal applied to the transparent support can be deposited by various methods. The film can be applied, for example, by chemical vapor deposition, vacuum evaporation, sputtering or the like. The metal film can, likewise, advantageously be applied on the transparent support in a film having different thickness configurations. For example, as shown in FIG. 1, a test piece 1 is illustrated which has a film of metal 20 of a uniform thickness deposited on the surface of a support 21. Another embodiment of a suitable test piece 2 is illustrated in FIG. 5, wherein a support 22 has a metal layer 23 deposited on the surface thereof in a step-like configuration. A still further embodiment of a suitable test piece 3 is shown in FIG. 10, which has the metal film 24 applied in a wedge-shaped layer on the support 25. There are other embodiments of the test pieces which can likewise be utilized in the present invention for obtaining certain specific types of information such as the test piece 4 illustrated in FIG. 13 in which the metal film 26 is applied in both a step-like configuration and in the form of separate, spaced-apart strips on the support 27.

In order to more fully explain the method of this invention, specific reference will be made to the use of the test piece 1 of FIG. 1. In conducting the evaluation of the soldering in accordance with this invention, the test piece 1, having the metal film 20 on its surface of the support 21, is placed in the pool of solder to be evaluated with the metal side 20 in contact with the molten solder pool. The metal film 20 is optically observed through the transparent support 21. The measurement of the time is started from the point the metal film 20 is brought into contact with the molten solder pool. When using, for example, a copper-metal film 20, the color observed at the start of the test will be a reddish copper color. As the test proceeds, the tin atoms of the solder will diffuse into the copper film and form copper-tin alloys. If the contact time is sufficiently long, the entire thicknesses of the film of copper 20 will be converted into an inter-metallic layer 28 comprised of alloys of the formula $Cu_3Sn$ or $Cu_6Sn_5$. As the alloying process continues, the color as viewed through the transparent support 21 will change from the reddish color of copper film to a bright, lustrous white metallic color of the intermetallic layer 28. This is the first endpoint with regards to determining the solderability properties. When the color change occurs, the time is recorded for comparison to known data. If contact of the metal film 28 with the solder pool is continued, a second endpoint will be reached, where as a result of the copper alloying and dissolving into the solder, and the lack of adhesion of the alloys to the support 21, the film of metal 28 on the support will be completely removed and a clear support 29, free of a metal layer, will be obtained. The time to reach this endpoint is likewise to be recorded as part of the test procedure. The time required for the initial color change and complete removal of the metal film from the support 21 are directly related to the solderability properties of the solder under evaluation.

The test method for the present invention is relatively simple to perform. There are, however, a number of variables in the test method which are required to be carefully controlled in order to obtain consistent results. The first variable is the thickness of the metal film on the support used for the evaluation. The thicker the film of metal on the support used for the evaluation, the longer will be the time required for the change in color due to alloying to become apparent through the transparent support. As can be seen in FIG. 15, there is a direct relationship between the thickness of the metal layer on the support and the time required for the color change to be noted through the transparent support. The solid line on the graph of FIG. 15 was obtained with a solder made from 60% virgin tin and 40% virgin lead. Satisfactory results can be obtained in a reasonable amount of time with film having a thickness from about 1-10 μm. A good optimum thickness for most test purposes is about 5 μm.

A further variable which must be controlled in order to obtain consistent results is the flow rate of the solder past the test pieces. The reaction which results in the alloying and color change is the result of the exchange of metal atoms at the interface of the metal film and the molten solder. If the method is conducted under relatively static flow conditions, there will be a relatively high concentration of the various metal atoms at the interface which will result in a reduction in the rate of alloying at the interface. Furthermore, since the presence of copper in the solder is a material factor in determining the solderability properties of the solder, the entire sample of solder under evaluation should be circulated past the test piece so that the test results will be representative of the entire batch of solder. The flow rate is measured as the rate of speed of the solder flow past the test piece. As shown in FIG. 16, the speed of the solder flowing past the test sample has a marked effect on the time required for alloying to occur. A flow speed of about 11 cm./second was found to be about optimum.

A third variable which must be controlled is the temperature of the molten solder. This variable by far has the greatest effect on the rate of alloying observed in the test procedure. As shown in FIG. 17 by the solid line, the time required for alloying of a solder can be distinctly different depending upon the temperature of the molten solder. For the purposes of conducting the test, a temperature of about 260° C. is considered optimum as this is a temperature which is commonly used in the soldering of electronic circuit boards.

The evaluation of the solder compositions can be conducted by different procedures, depending, to some extent, on the properties desired to be evaluated and the type of test piece utilized for the evaluation. The time required for the color change and for the complete dissolution of the metal film from the support can be both measured to obtain comparative values. The test piece 1 of FIG. 1 is especially useful for this type of evaluation. The test piece 1, having a copper-colored metal film 20, is held in contact with the molten solder until a white metal layer 28 is observed and, if desired, the test is continued until the white metal layer 28 completely dissolves to provide a clear support 29.

It is also possible to use a standard fixed length of time to conduct the evaluation and, thereby, determine the rate of alloying by way of a scale or similar means. The test piece 3 of FIG. 10 is especially useful for fixed-time evaluation. The test piece 3 is immersed in the solder pool for a fixed period of time and then removed from the pool and immediately quenched to prevent further alloying. The test piece 30, after contact with the molten solder, is viewed through the transparent support 25. There should preferably be three different zones, 31, 32, 33, which can be optically distinguished. These zones are a red zone 31, which is the unchanged metal film a white metallic alloy zone 32 and a zone 33 which is clear, indicating complete removal of the alloy. By providing a scale 34 or by measuring the amount of the alloying for a given length of time, it is possible to obtain an accurate evaluation of the solderability quality of a given solder.

The substrate 2 in FIG. 5 can be used in both timed or fixed-length tests, and the results are reported by noting the changes as seen in FIGS. 6, 7, 8 and 9. As the test is conducted as seen in FIG. 7, the zone 1 on the FIG. 7 will change to a white alloyed color. As the test is continued, the zone 1 will dissolve the solder and zone 2 will change into a white-colored alloy. At completion of the test, there will be complete removal of all of the metal, giving the clear support as shown in FIG. 9. By measuring the time required for each of the changes, it is possible to accurately obtain the evaluation of the solderability of a given solder composition.

The test piece 4, illustrated in FIGS. 13 and 14 can be used to conduct a plurality of tests. Because of the stepped configuration of the metal layer 27, the time for alloying or dissolving can be measured as noted above. However, because of the presence of the spaced apart strips of metal 26, the test piece 4 can also be used to measure the icicling or bridging properties by allowing the solder to flow on one test piece 4 in the same direction as the line of metal 26 and in a second test by allowing the solder to flow at right angles to the strips of metal 26. By comparison of the amount of bridging and icicling between the two test pieces, and possibly by comparison with known standards, an objective evaluation of these additional properties can be obtained.

In addition to using the method of the present invention for evaluating solders, the test method for this invention can also be used to evaluate fluxes, soldering oils and the like as well as different types of solder compositions. Furthermore, changes in the process conditions, such as changes in the temperature, flow rate, rate of soldering and the like can likewise be evaluated with the test method of the present invention. The test method of the present invention can also be advantageously used as a quality control method to establish purchase quality standards for solder compositions and the like. The tests conducted according to the present invention give fast, accurate and reproducible results directly related to the solderability properties such that an objective quality standard can readily be established by using the test procedure of this invention.

Other variations can be made in the test procedure such as modifying the time, the structure of the substrates and the like and such changes are likewise included in the scope of the present invention.

The following examples are given by way of further illustration of the present invention and are not intended to limit the scope of the present invention beyond the scope of the subjoined claims. All percentages are in percentages by weight and temperatures in degrees centigrade unless otherwise indicated.

EXAMPLE 1

Part A: A series of test pieces were prepared in the following manner.

Borosilicate glass was used as a support material. The size of the supports were 24 mm. in length, 6 mm. in width, and about 0.2 mm. (0.17–0.25 mm.) in thickness. The glass supports, prior to metallization, were cleaned several times with trichloroethylene and then dried in air. The cleaned supports were kept in a dessicator.

A conventional evaporator was used to vacuum evaporate a thin film of copper onto the borosilicate glass supports. A vacuum is maintained at about $4 \times 10^{-7}$ Torr. The substrates were heated with a halogen heat lamp to about 100° C. for three hours. Evaporation was started twenty minutes after the heat lamp was turned off. The source copper was charged onto a source heater. Electric power of about 100 to 150 w. was supplied to the source heater and a deposition rate was established at about 0.2 $\mu$m/min. The copper evaporation was performed using a photo-resist mask and the resulting film size was maintained at about 15 mm. long, 2.5 mm. wide, and a time deposition was varied in order to obtain a series of test pieces having thicknesses of metal from 1–10 $\mu$m in thickness. The thickness of the individual substrates was monitored with a quartz crystal thickness monitor. To verify the actual film thickness and the monitored film thickness, the mass of the samples were measured with a micro-balance before and after evaporation. After each substrate was prepared, the surface thereof was almost immediately protected with a preflux (Tamura B111B) to protect the copper layer from oxidation. Before the samples were subjected to the test, however, the preflux was removed and a solder flux (Tamura Y-20) was applied to the samples.

All of the substrates were optically examined before utilization in the test and were found to have a bright red copper color when viewed through the glass support. Furthermore, each of the layers of copper applied to the substrates were further checked for adhesion to the glass supports and were found to be well-adhered to the support. The test pieces were preserved for use in the examples described below.

Part B: An experimental test apparatus was assembled which consisted of a heater for the solder bath and a stirrer to generate a known rate for the molten solder under evaluation.

A mantle heater (rated wattage 400 w.) was employed as the heater which had an inside space 9.5 cm. in depth and 7.1 cm. in diameter. A test solder bath, which was 2 cm. in height and 6 cm. in diameter, was established in the receptacle in the mantle heater. An inlet means was provided for maintaining a layer of nitrogen over the test sample in order to prevent surface oxidation of the solder samples.

The solder temperature and the ambient temperature were measured with thermocouples. For this particular experiment, the observed solder temperature fluctuation was maintained at ±1° at a soldering temperature of 260°, which is a typical soldering temperature encountered in the manufacture of electronic assemblies.

To determine the effect of solder flow on the test results, the solder was stirred at various speeds. A stirrer blade was provided in the bath of the molten solder. The blade was rotated about a vertical axis with a direct current motor-driven shaft. The flow speed of the solder across the surface of the test specimens was calculated from the rotational speed of the stirrer and the distance of the sample from the stirrer shaft.

The test apparatus was charged with a fresh sample of the solder, comprised of 60% virgin tin and 40% virgin lead. This particular solder composition is the most common type of solder utilized in the manufacture of electronic assemblies.

The virgin bath of solder was tested at different flow speeds to determine the effect of the solder flow on the results obtained in the tests. The measured time was taken as that required to complete the color change over the entire area of the metallic film applied to the support.

FIG. 16 shows the relationship of the color change time to the flow speed of the solder across the sample. For purposes of the test, the solder temperature was maintained at a constant 260° C. and the substrates employed in the tests had a film thickness of metal applied thereto which was 5 $\mu$m in thickness.

EXAMPLE 2

Using the test apparatus as described in Example 1, the effect of thickness of the metal film layer was evaluated with regard to the length of time required for the color change to occur due to alloying of the solder with the metal. The solder bath was maintained at a temperature of 260°±1 and the solder flow was maintained at a rate of 11 cm./sec. past the test pieces. A series of test pieces, having metal thicknesses varying between 1 $\mu$m and 10 $\mu$m prepared in Example 1 was used in the evaluation.

The evaluation was conducted utilizing two different batches of solder. The first batch was a fresh batch of solder which was comprised of 60% virgin tin and 40% virgin lead. The second batch was a batch of solder which initially had the same composition, namely 60% tin and 40% lead, but which had been used in a mass soldering process and had become contaminated and was found to have reduced solderability properties. The two samples were evaluated against each other to determine the difference, if any, which could be observed between the samples of the solder.

FIG. 15 shows the dependency of the copper film thickness on the test results obtained. The results obtained with the fresh solder (solid line) and the contaminated solder (dotted line) are shown on FIG. 16. In both evaluations, the soldering temperature was maintained at 260° C.±1° and the rotation speeds were maintained at a speed corresponding to a solder flow of 11 cm./sec.

EXAMPLE 3

Using the test apparatus as described in Example 2, the effect of temperature on the test results was determined. In order to conduct the test, the test pieces provided for this purpose had a 5 μm thickness metal layer and the solder flow speeds was maintained at 11 cm./sec. In this test, two batches of solder were evaluated, namely a virgin batch of solder comprised of 60% tin and 40% lead (shown by the solid line) and a contaminated batch of solder (shown by the dotted line). The results are reported on the graph of FIG. 17.

EXAMPLE 4

In order to determine the effect of copper as a contaminant in the solder compositions used in mass soldering, a number of solder compositions were prepared utilizing virgin metals in order to produce various combinations of tin, lead and measured amounts of copper. The results of this test with respect to the solderability, as exhibited by the test method of this invention, are listed below. Included in the results are the test results obtained with the contaminated solder from the mass soldering process. The soldering temperatures for the test procedure were maintained at 260° C.±1°, the copper film thickness was 5 μm, and the solder flow rate was maintained at a speed of 11 cm./sec. The following results were obtained:

| Copper Content Weight/% | Time for Color Change |
| --- | --- |
| 0 (virgin solder) | 18 seconds |
| 0.100 | 30 seconds |
| used solder | 64 seconds |
| 0.300 | 87 seconds |
| 0.500 | 680 seconds |

EXAMPLE 5

In order to determine the validity of the method of the present invention, a test piece having a 5 μm layer of copper was placed in contact with the surface of a virgin solder comprised of 60% tine and 40% lead and held in contact until the color change was started to be observed through the support. The sample was, however, removed before the layer had changed from the characteristic red to white color of the alloy. The samples were then immediately quenched.

The copper solder alloy content was then analyzed by X-ray. In the samples in which the backside was mostly changed, but where the original copper color slightly remained after quenching of the test piece, the chemical phases were found to vary from that of pure copper at the glass surface to various alloys of copper and tin as the analysis proceeded outwardly from the interface of the substrate and the copper. The residual film was ultrasonically peeled from the substrate and analyzed with an X-ray diffractometer. The diffraction peaks corresponded to $Cu_3Sn$ and $Cu_6Sn_5$ along with the corresponding peaks indicating copper, tin and lead.

We claim:

1. The method for evaluating the solderability properties of a molten solder, said method comprising the steps of
   (a) providing a test piece having a transparent support with first and second surfaces, and having a metal film of a predetermined thickness formed on the first surface, said metal of the metal film being a metal which will alloy with the molten solder, said second surface be positioned relative to the first surface so that the area of the metal film on the first surface can be observed through the transparent support from the second surface;
   (b) placing the metal film in contact with the molten solder;
   (c) maintaining the metal film in contact with the molten solder for a measured length of time, at least sufficiently long enough for noticeable change due to alloying of the molten solder with the metal of the metal film to occur and be observed through the transparent support from second surface;
   whereby, a rate of alloying of the molten solder with the predetermined thickness of the metal film is obtained which rate is directly related to the solderability properties of the molten solder.

2. The method according to claim 1 wherein the metal film has a first color as formed on the support and a second color when alloyed with the molten solder.

3. The method according to claim 2 wherein the metal is copper.

4. The method according to claim 2 wherein the metal is gold.

5. The method according to claim 2 wherein the time is measured from the time the metal film enters the molten solder until a color change due to alloying is observed at the first surface as viewed through the transparent support from the second surface.

6. The method according to claim 1 wherein the time is measured from the time the metal film enters the molten solder until the predetermined thickness of metal film on the support alloys with and dissolves into the molten solder.

7. The method according to claim 1 wherein the transparent support is about 0.20 to about 0.30 mm. in thickness.

8. The method according to claim 7 wherein the transparent support is made of borosilicate glass.

9. The method according to claim 1 wherein the film of metal is applied in a uniform thickness layer.

10. The method according to claim 9 wherein the predetermined thickness is about 5 μm.

11. The method according to claim 1 wherein the metal film is applied in a film of predetermined increasing thickness.

12. The method according to claim 11 wherein the testpiece with the film of predetermined increasing thickness is immersed in the molten solder for a fixed period of time and the amount of alloying observable through the transparent support on the second surface relative to the thickness of the metal film is measured to determine the rate of alloying.

13. The method according to claim 1 wherein the molten solder is circulated past the metal film.

14. The method according to claim 13 wherein the molten solder is circulated past the film of metal at a rate of about 11 cm./sec.

15. The method according to claim 1 wherein the molten solder is maintained at a temperature of about 260° C.

* * * * *